US00PP33978P2

(12) United States Plant Patent
Jan Kraan

(10) Patent No.: US PP33,978 P2
(45) Date of Patent: Mar. 1, 2022

(54) ***DIERVILLA* PLANT NAMED 'BOCOFIRE'**

(50) Latin Name: ***Diervilla* hybrid**
Varietal Denomination: Bokofire

(71) Applicant: Kees Jan Kraan, Alphen aan den Rijn (NL)

(72) Inventor: Kees Jan Kraan, Alphen aan den Rijn (NL)

(73) Assignee: BOOT & CO BOOMKWEKERIJEN BV, Boskoop (NL)

( * ) Notice: Subject to any disclaimer, the term of this patent is extended or adjusted under 35 U.S.C. 154(b) by 0 days.

(21) Appl. No.: 17/386,152

(22) Filed: Jul. 27, 2021

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Penny J. Aguirre

(57) ABSTRACT

A new cultivar of *Diervilla* hybrid plant named 'Bocofire' that is characterized by its compact plant habit, its dome plant shape, its young foliage that is orange in color that changes to yellow in color when maturing and changes to yellow to yellow-green in color when fully mature.

2 Drawing Sheets

Botanical classification: *Diervilla* hybrid.
Variety denomination: 'BOCOFIRE'.

BACKGROUND OF THE INVENTION

The present invention relates to a new and distinct cultivar of *Diervilla* of hybrid origin and will be referred to hereafter by its cultivar name, 'BOCOFIRE'. 'Bokofire' is a new cultivar of bush honeysuckle grown for use as a landscape plant.

The new cultivar of *Diervilla* arose from a breeding program conducted by the Inventor in Boskoop, The Netherlands with the goal of developing a *Diervilla* cultivar with more leaf color variation, a compact habit and dome plant shape.

'BOCOFIRE' originated as a seedling that arose from seed planted from open pollination of *Diervilla splendens* 'El Madrigal' (U.S. Plant Pat. No. 28,060) in July of 2015. The female plant was surrounded by numerous varieties and species of *Diervilla*; the male parent is unknown. 'BOCOFIRE' was selected as a single unique plant in summer of 2018 from amongst the resulting seedlings.

Asexual propagation of the new cultivar was first accomplished by the inventor using stem cuttings in summer of 2017 in Boskoop, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bokofire' as a unique cultivar of *Diervilla*.

1. 'BOCOFIRE' exhibits a compact plant habit.
2. 'BOCOFIRE' exhibits a dome plant shape.

3. 'BOCOFIRE' exhibits young foliage that is orange in color that changes to yellow in color when maturing and changes to yellow to yellow-green in color when fully mature.

The female parent plant of 'BOCOFIRE' differs from 'BOCOFIRE' in having brown-red foliage colors that change to black-purple in color when maturing in late summer and leaves that are broader in width. 'BOCOFIRE' can be compared to *Diervilla rivularis* 'Diwibru01' (U.S. Plant Pat. No. 27,932), and *Diervilla* 'G2X88544' (U.S. Plant Pat. No. 27,548). 'Diwibru01' is similar to 'BOCOFIRE' in having leaves that are yellow in color. 'Diwibru01' differs from 'BOCOFIRE' in having leaves that are more narrow in shape with tips that is more pointed, young leaves that are yellow in color and slightly tinged with orange and in having a more upright plant habit, and less wide plant shape. 'G2X88544' is similar to 'Bokofire' in having a compact plant habit. 'G2X88544' differs from 'BOCOFIRE' in having young leaves that are light brown-red to dark bronze in color changing to red-green in color with maturing and then changing to green and slightly tinged with red in late summer.

BRIEF DESCRIPTION OF THE DRAWINGS

The accompanying color photographs illustrate the overall appearance and distinct characteristics of the new *Diervilla*. The photographs were taken of a three year-old plant of the new cultivar as grown outdoors in a 5-liter container in Boskoop, The Netherlands.

The photograph in FIG. 1 illustrates the overall appearance of 'BOCOFIRE'.

Figure 1:
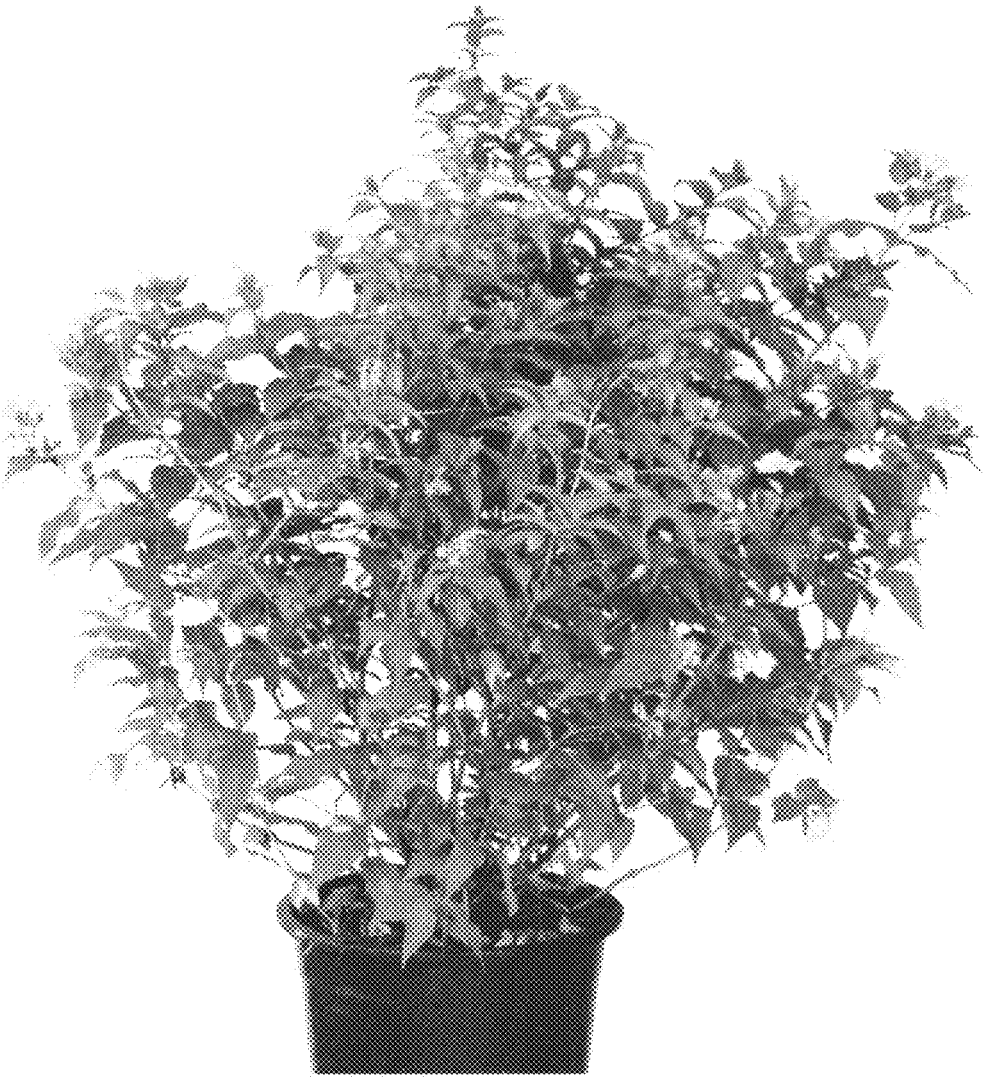
Figure 2:
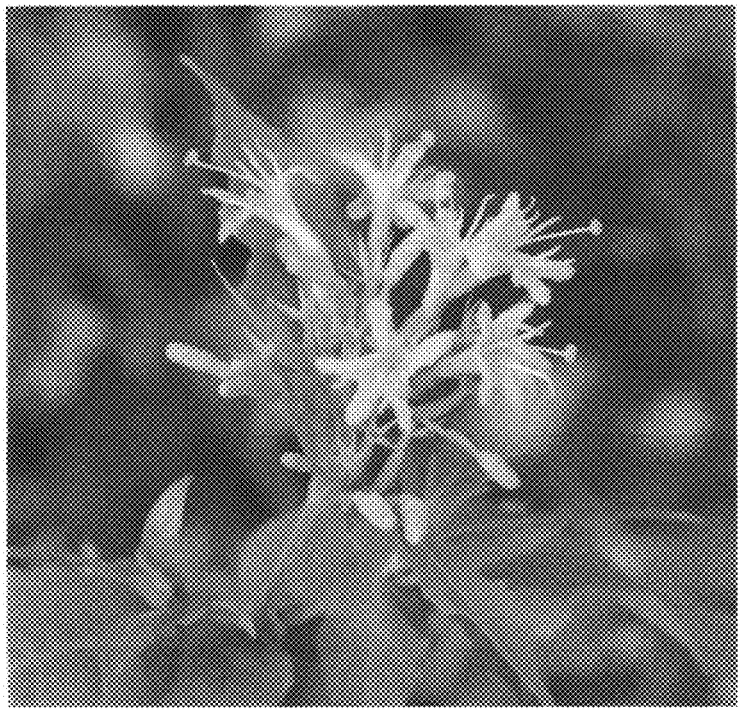

The photograph in FIG. 2 is a close-up view of an inflorescence of 'BOCOFIRE'.

Figure 3:
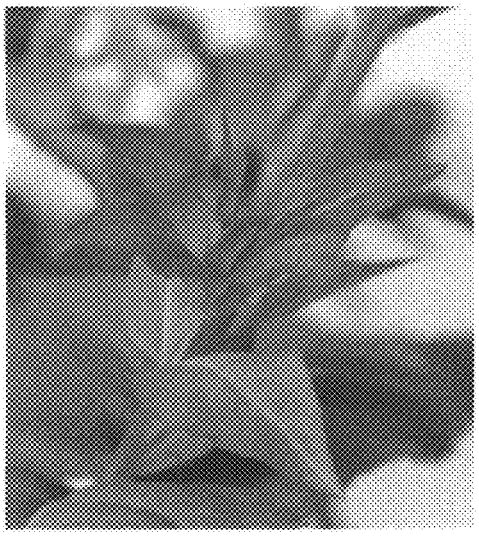

The photograph in FIG. 3 provides a close-up view of the young foliage of 'BOCOFIRE'.

Figure 4:
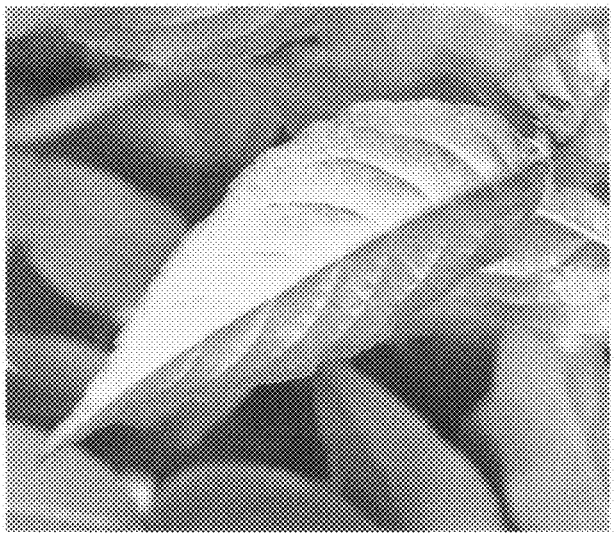

The photograph in FIG. 4 provides a close-up view of the mature foliage of 'BOCOFIRE'.

The colors in the photographs are as close as possible with the digital photography techniques available, the color values cited in the detailed botanical description accurately describe the colors of the new *Diervilla*.

DETAILED BOTANICAL DESCRIPTION

The following is a detailed description of three year-old plants of the new cultivar as grown outdoors in a 5-liter containers in Boskoop, The Netherlands The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms for 6 weeks from late June to mid-August in The Netherlands.

*Plant type*.—Perennial, deciduous shrub.

*Plant habit*.—Compact and dome-shaped.

*Height and spread*.—Average of 89.2 cm in height and 105.6 cm in width as a 2-month old plant, reaches an average of 1.2 m in height and 1.5 m in spread as a mature plant in the landscape.

*Hardiness*.—At least in U.S.D.A. Zones 4 to 8.

*Diseases and pests*.—No susceptability or resistance to diseases or pests has been observed.

*Propagation*.—Stem cuttings.

*Root description*.—Fibrous.

*Root development*.—Roots develop in 14 to 21 days in summer an fully develop as a young rooted plant in 3 months.

*Growth rate*.—Moderate to vigorous.

Branch description:

*Shape*.—Nearly quadrangular, angled with four ribs.

*Branch color*.—Young stems; 145A with upper surface tinged 165B, mature stems; upper surface 176A, lower surface145B, older bark; N199A, N199B, 200D and N200A and N200B.

*Branch size*.—An average of 34.5 cm in length (excluding inflorescence) and 3 mm in width.

*Stem surface*.—Very slightly glossy and sparsely covered with very short hairs; an average of 0.2 mm in length and too small to measure color.

*Branch aspect*.—Upward and outward.

*Branch strength*.—Very strong.

*Internode length*.—Average of 5.6 cm.

*Branching*.—An average of 23 primary branches, 125 secondary branches.

Foliage description:

*Leaf shape*.—Ovate to narrow ovate.

*Leaf division*.—Simple.

*Leaf base*.—Truncate.

*Leaf apex*.—Long apiculate.

*Leaf venation*.—Pinnate, upper veins color; 151C, strongly tinged N170C to N170D, changing to 144B in late summer, lower veins color; 151C, changing to 145A in late summer.

*Leaf margins*.—Finely serrate.

*Leaf arrangement*.—Opposite.

*Leaf attachment*.—Sessile.

*Leaf surface*.—Upper surface; very slightly glossy, smooth, sparsely pubescent, except for densely pubescent main vein, hairs an average of 0.2 mm in length, too small to measure color, lower surface; moderately glossy, smooth, sparsely pubescent on secondary veins 0.2 mm in length, too small to measure color.

*Leaf size*.—Average of 11.1 cm in length and 5.1 cm in width.

*Leaf quantity*.—Average of 16 leaves (8 pairs) per branch.

*Leaf color*.—Young upper surface; 175A, young lower surface; 176A and 178A, mature upper surface; 153D, margins 173A to 173B, changing to 137B in late summer, mature lower surface; 146B and 151B to 151C, margins 173B, changing to 146B in late summer.

*Petioles*.—Strong, average of 3.5 mm in length and 2 mm in width, both surfaces 144B in color, surface glabrous, moderately glossy.

*Stipules*.—Not present.

Inflorescence description:

*Inflorescence type*.—Terminal and axillary compound cymes of tubular flowers.

*Inflorescence size*.—Average of 5.1 cm in height and 5.8 cm in width.

*Flower fragrance*.—None.

*Lastingness of inflorescence*.—Average of one week, self-cleaning.

*Flower quantity*.—Average of 28 flowers per terminal cyme, average of 625 flowers per plant.

*Flower type*.—Single, campanulate with tubular base.

*Flower size*.—Average of 1.1 cm in diameter (horizontal), 1.4 cm in diameter (vertical), 2.5 cm in depth (length), throat diameter 3 mm, flower tube length 9 mm, flower tube diameter 3.5 mm.

*Flower aspect*.—Upward to outward.

*Flower buds*.—Narrow oblong, slightly curved in shape, average of 1.7 cm in length and 3 mm in diameter, surface is matte, smooth and very slightly rugose, color a blend of 1A and 2A, immature tube 1B, base N148B, sunny side tinged 176B.

*Peduncles*.—Strong, held in an average angle of 30°, average of 1.5 cm in length and 1.5 mm in diameter, 146B in color, surface is matte, nearly quadrangular in shape, angled with four ribs, moderately to densely covered with very short soft pubescence; an average of 0.2 mm in length, too small to measure color.

*Pedicels*.—Moderately strong, held in an average angle of 20°, average of 2 mm in length and 0.75 mm in diameter, 146B in color, surface is matte, nearly quadrangular in shape, angled with four ribs, moderately to densely covered with very short soft pubescence; an average of 0.2 mm in length, too small to measure color.

*Calyx*.—Rotate in shape, average of 3 mm in length and 2 mm in diameter, surface texture glabrous.

*Sepals*.—5, 1 whorl, lanceolate in shape, narrow acuminate apex, base fused and broad cuneate, smooth and matte on both surfaces, lower surface sparsely covered with very short hairs, average of 0.2 mm in length, too small to measure color, entire margin, average of 3 mm in length and 0.75 mm in width, color: when opening upper and lower surface; 145B, when fully open upper and lower surface; 145A.

*Petals.*—5, 1 whorl, rotate with 5 lobes with lower 55% of petal is fused into tube making a campanulate shape, both surfaces are matte and glabrous with only the lower corolla lobe having sparse short, soft hairs; an average of 0.5 mm in length and too small to measure color, lobes; narrow oblong in shape, entire margin, obtuse to broad acute apex, average of 1.6 cm in length and 3 mm in width, color: upper surface when opening; 150B and 1A, lower lobe 6A, lower surface when opening; 3B, upper surface when fully open; a blend of 150B and 1A, changing to 22B and 24B, lower lobe 5B, lower surface when fully open; 3B, fading to 11A, throat and tube color; a blend of 150B and 1A.

Reproductive organs:

*Gynoecium.*—Pistil; 1, average of 1.9 cm in length, style; 1.7 cm in length and 145C in color, stigma; club-shaped, 146D in color, ovary; 143C, top tinged 174A in color.

*Androcoecium.*—Stamens; 5, implanted in the tube, filaments; 150D in color and 7 mm in length, anthers; 3.5 mm in length and 20A in color, narrow oblong in shape, dorsifixed, pollen is low in quantity and 20B in color.

*Fruit and seed.*—No fruit or seed has been observed to date.

It is claimed:

1. A new and distinct cultivar of *Diervilla* plant named 'Bocofire' as herein illustrated and described.

* * * * *